US011219409B2

(12) United States Patent
Kwak et al.

(10) Patent No.: US 11,219,409 B2
(45) Date of Patent: Jan. 11, 2022

(54) METHOD AND SYSTEM FOR USER INTERACTION THROUGH USER POSTURE RECOGNITION

(71) Applicant: Morethings Co., Ltd., Yongin-si (KR)

(72) Inventors: Jae Kyung Kwak, Yongin-si (KR); Kwang Dek An, Hwaseong-si (KR); Ji Won Oh, Gwangju-si (KR); Hwan Il Park, Seoul (KR); Jeong Min Han, Seoul (KR)

(73) Assignee: Morethings Co., Ltd., Yongin-si (KR)

( * ) Notice: Subject to any disclaimer, the term of this patent is extended or adjusted under 35 U.S.C. 154(b) by 34 days.

(21) Appl. No.: 16/998,416

(22) Filed: Aug. 20, 2020

(65) Prior Publication Data

US 2020/0405221 A1 Dec. 31, 2020

Related U.S. Application Data

(63) Continuation of application No. PCT/KR2018/014731, filed on Nov. 27, 2018.

(30) Foreign Application Priority Data

Feb. 21, 2018 (KR) ........................ 10-2018-0020389

(51) Int. Cl.
*A61B 5/00* (2006.01)
*G16H 20/30* (2018.01)
(Continued)

(52) U.S. Cl.
CPC ............ *A61B 5/486* (2013.01); *A61B 5/4561* (2013.01); *A61B 5/6891* (2013.01); *A61B 5/742* (2013.01);
(Continued)

(58) Field of Classification Search
CPC ..... A61B 5/486; A61B 5/4561; A61B 5/6891; A61B 5/742; G06F 3/011; G06Q 10/1095;
(Continued)

(56) References Cited

U.S. PATENT DOCUMENTS

| 2011/0275939 | A1* | 11/2011 | Walsh | G09B 19/003 600/473 |
| 2016/0183687 | A1* | 6/2016 | Hoyt | A47C 31/126 297/217.2 |
| 2019/0175076 | A1* | 6/2019 | Lustig | A61B 5/7455 |

* cited by examiner

*Primary Examiner* — Michael C Grant
(74) *Attorney, Agent, or Firm* — Studebaker & Brackett PC

(57) ABSTRACT

An user interaction system for performing interaction with a user based on recognition of a sitting posture of the user includes a posture recognition seat including a posture recognition sensor for recognition the sitting posture of the user, and at least one communication module for communication with an external device, a posture mimicking animated device including a communication module for performing communication with the communication module of the posture recognition seat, wherein the posture mimicking animated device visually mimics the sitting posture of the user or visually or audibly guide the sitting posture of the user, in accordance with state information about the sitting posture of the user determined based on a sensing result obtained by the posture recognition sensor, and a mobile application installed in a communication device possessed by the user, wherein the mobile application receives synchronized information related to the sitting posture of the user via communication with the posture recognition seat, and generates user interaction information corresponding to the received information and displays the user interaction information on an application screen.

3 Claims, 14 Drawing Sheets

(51) Int. Cl.
*G16H 40/67* (2018.01)
*H04M 1/72427* (2021.01)
*G06F 3/01* (2006.01)
*G06Q 10/10* (2012.01)
*G06T 13/40* (2011.01)
*G06T 13/80* (2011.01)
*G08B 5/22* (2006.01)
*G09B 19/00* (2006.01)
*H04W 4/80* (2018.01)

(52) U.S. Cl.
CPC ......... *G06F 3/011* (2013.01); *G06Q 10/1095* (2013.01); *G06T 13/40* (2013.01); *G06T 13/80* (2013.01); *G08B 5/22* (2013.01); *G09B 19/00* (2013.01); *G16H 20/30* (2018.01); *G16H 40/67* (2018.01); *H04M 1/72427* (2021.01); *A61B 2562/0247* (2013.01); *A61B 2562/04* (2013.01); *H04W 4/80* (2018.02)

(58) Field of Classification Search
CPC ......... G06T 13/00; G06T 13/40; G06T 13/80; G08B 5/22; G09B 19/00; G16H 40/63; G16H 20/70; G16H 20/00; G16H 20/30; G16H 40/67; H04M 1/72403; H04M 1/72412; H04M 1/725; H04M 1/72427; H04W 4/80; H04W 4/00; A47C 31/126
USPC .................................................. 434/236, 247
See application file for complete search history.

METHOD AND SYSTEM FOR USER INTERACTION THROUGH USER POSTURE RECOGNITION

CROSS-REFERENCE TO RELATED APPLICATIONS

The present application is a continuation of International Patent Application No. PCT/KR2018/014731, filed on Nov. 27, 2018, which is based upon and claims the benefit of priority to Korean Patent Application No. 10-2018-0020389, filed on Feb. 21, 2018. The disclosures of the above-listed applications are hereby incorporated by reference herein in their entirety.

BACKGROUND

Embodiments of the inventive concept described herein relate to user interaction method and system, and more specifically, to user interaction method and system using a posture recognition seat and a posture mimicking animated device.

The number of people who received treatment for spinal diseases was 12.6 million in 2015, and 8.9 million in 2007 and thus has increased by 3.65 million for 7 years. The medical expenses they used for one year amounted to 3,875.5 billion won. The number of occurrences of the spinal disorders was 46.6 million in 2007 and was 87.9 million in 2014, and thus has increased by 88.4% (41.3 million) and thus the medical expense has increased by 95.2% (1,986 billion won→3,876.6 billion won).

Various schemes have been proposed to solve this spinal disease problem. However, it is inconvenient to use existing posture correction chairs, cushions, and bands because they physically and forcibly correct the user's posture. Thus, a frequency of use thereof gradually decreases. Further, it becomes difficult to achieve an correction effect when they are not in use. In addition, in the existing products, the user checks the user's posture through a smartphone application, thereby causing inconvenience. Due to the inconvenience, the user later checks the posture such that the user may not immediately check his or her posture.

SUMMARY

Embodiments of the inventive concept provide user interaction method and system in which the user's posture is recognized through a posture recognition seat including a sensor and then the recognized posture is immediately mimicked through a specific posture mimicking animated device, thereby to allow the user to recognize the posture currently taken by himself or herself in an audible or visual or vibration manner, and various interactions with the user is enabled using the posture recognition seat and the posture mimicking animated device.

According to an exemplary embodiment, a user interaction system for performing interaction with a user based on recognition of a sitting posture of the user includes a posture recognition seat including a posture recognition sensor for recognition the sitting posture of the user, and at least one communication module for communication with an external device, a posture mimicking animated device including a communication module for performing communication with the communication module of the posture recognition seat, wherein the posture mimicking animated device visually mimics the sitting posture of the user or visually or audibly guide the sitting posture of the user, in accordance with state information about the sitting posture of the user determined based on a sensing result obtained by the posture recognition sensor, and a mobile application installed in a communication device possessed by the user, wherein the mobile application receives synchronized information related to the sitting posture of the user via communication with the posture recognition seat, and generates user interaction information corresponding to the received information and displays the user interaction information on an application screen.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
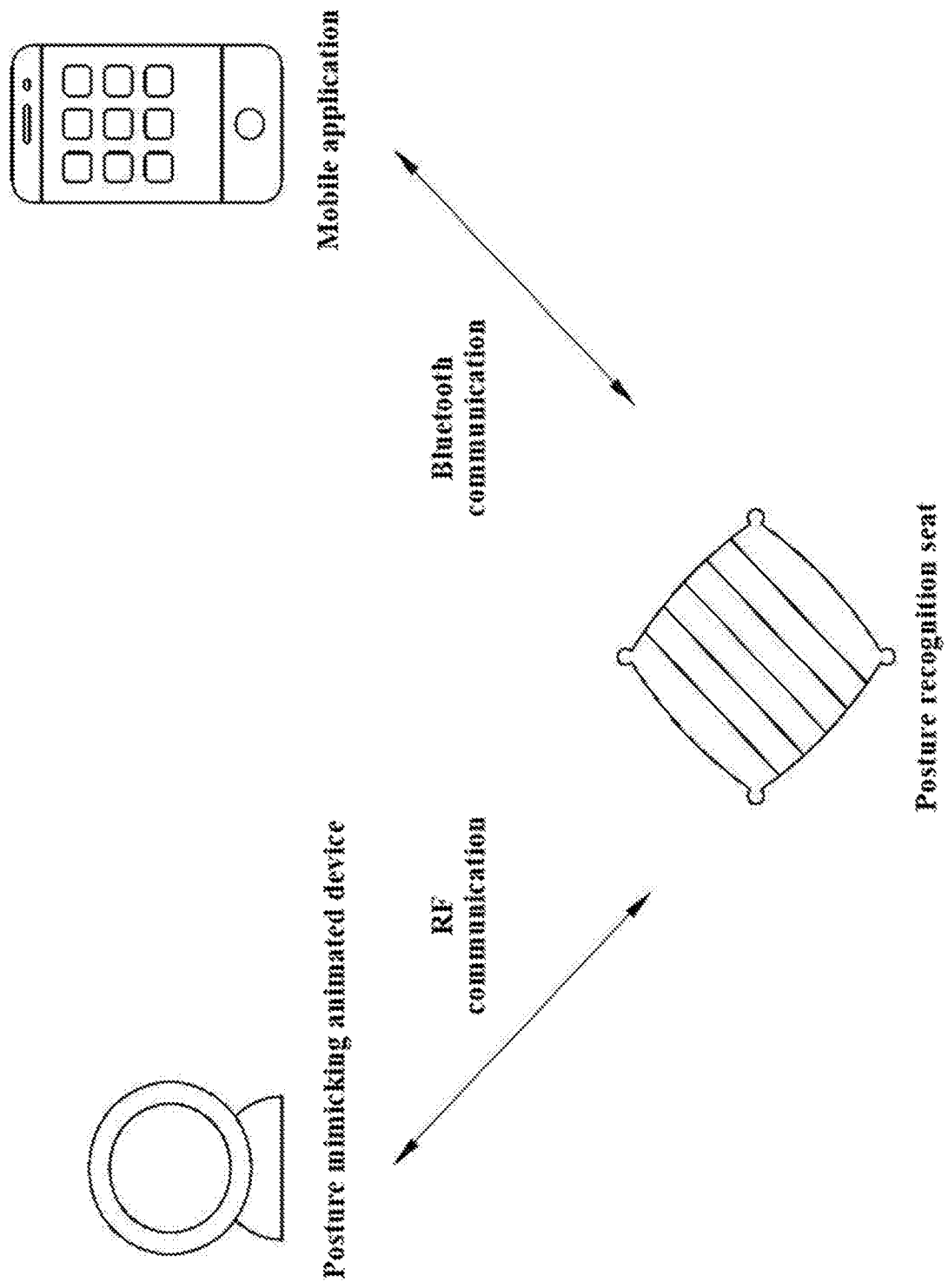
FIG. 1 to FIG. 2C are diagrams for generally describing user interaction method and system using a posture recognition seat and a posture mimicking animated device according to an embodiment of the inventive concept.

The inventive concept may have various modifications and various embodiments and thus may be intended to illustrate specific embodiments in the drawings and describe in detail in the detailed description. However, the embodiments are not intended to limit the inventive concept thereto, and rather the inventive concept should be understood to include all of modifications, equivalents, or substitutes included in the spirit and scope of the inventive concept.

In describing the inventive concept, when it is determined that a detailed description of related known components may unnecessarily obscure the subject matter of the inventive concept, the detailed description thereof will be omitted. Further, numbers (e.g., first, second, etc.) used in the description of the present specification are merely identification symbols for distinguishing one component from other components.

Further, in the present specification, when one component is referred to as "connected" or "coupled" to another component, one component may be directly connected or directly coupled to the other component. However, it should be understood that one component may be connected or coupled to another component via still another component therebetween unless otherwise indicated herein.

Further, in the present specification, when a device "includes" a specific component, it means that other components may be further included in the device unless otherwise stated, rather than excluding other components. Further, a term such as "unit" or "module" described in the specification mean a unit that processes at least one function or operation, and means that the unit or module may be implemented as one or more hardware or software, or a combination of hardware and software.

Figure 2A:
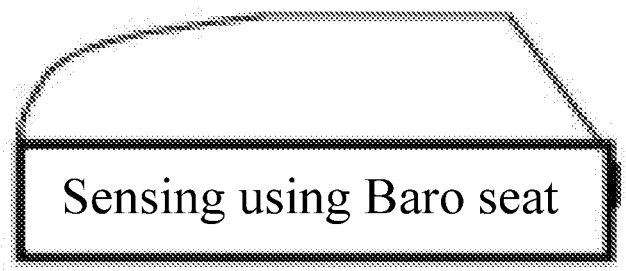
Figure 2B:
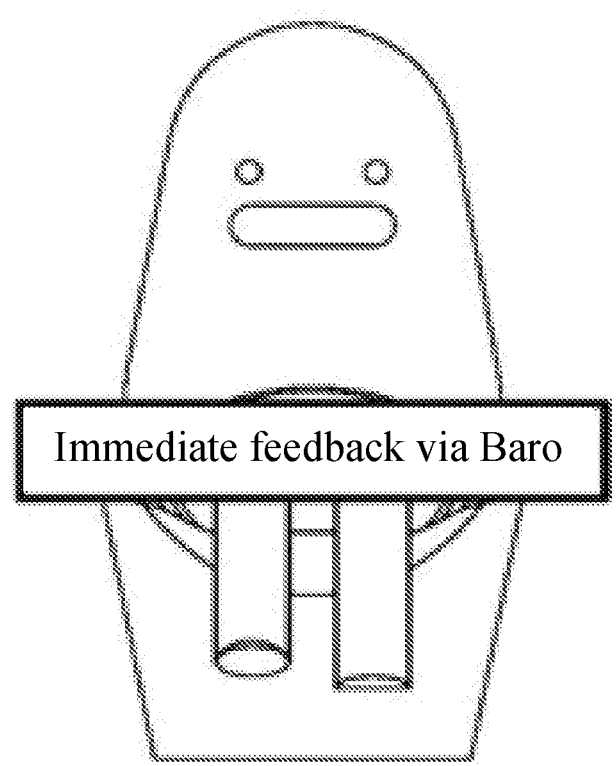
Figure 2C:
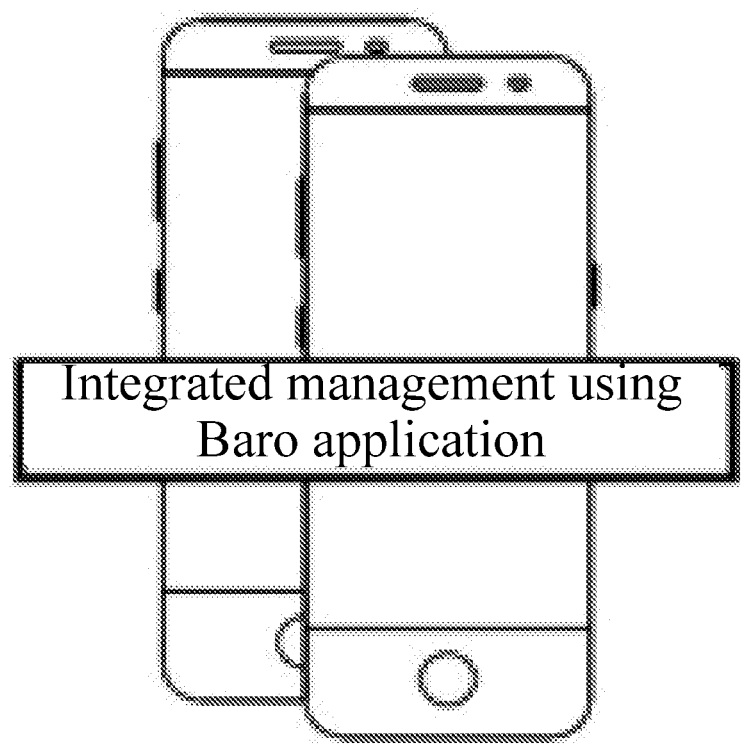
Figure 3:
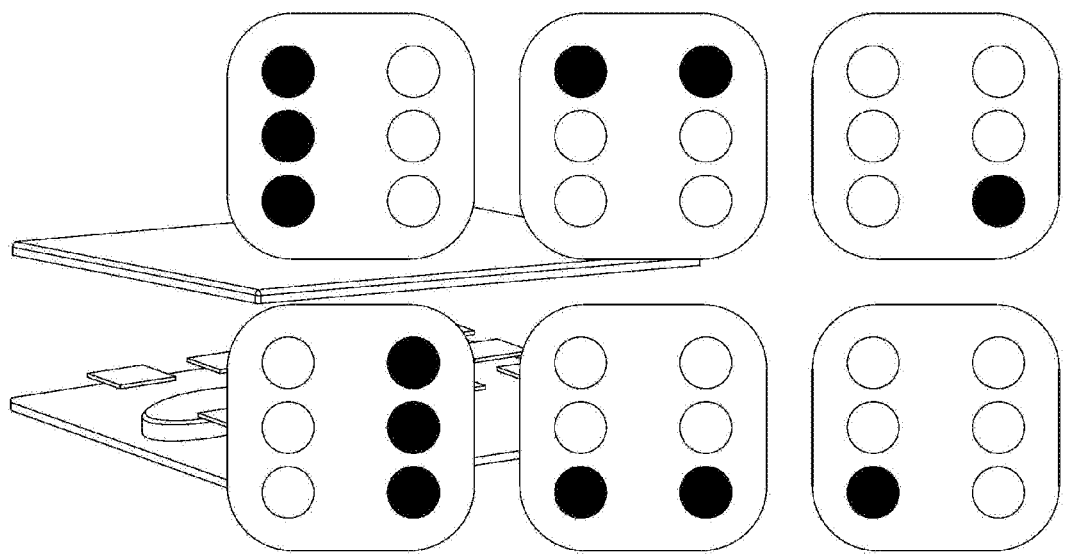
FIG. 3 is a reference diagram for describing a user posture recognition scheme via a posture recognition seat.
Figure 12:
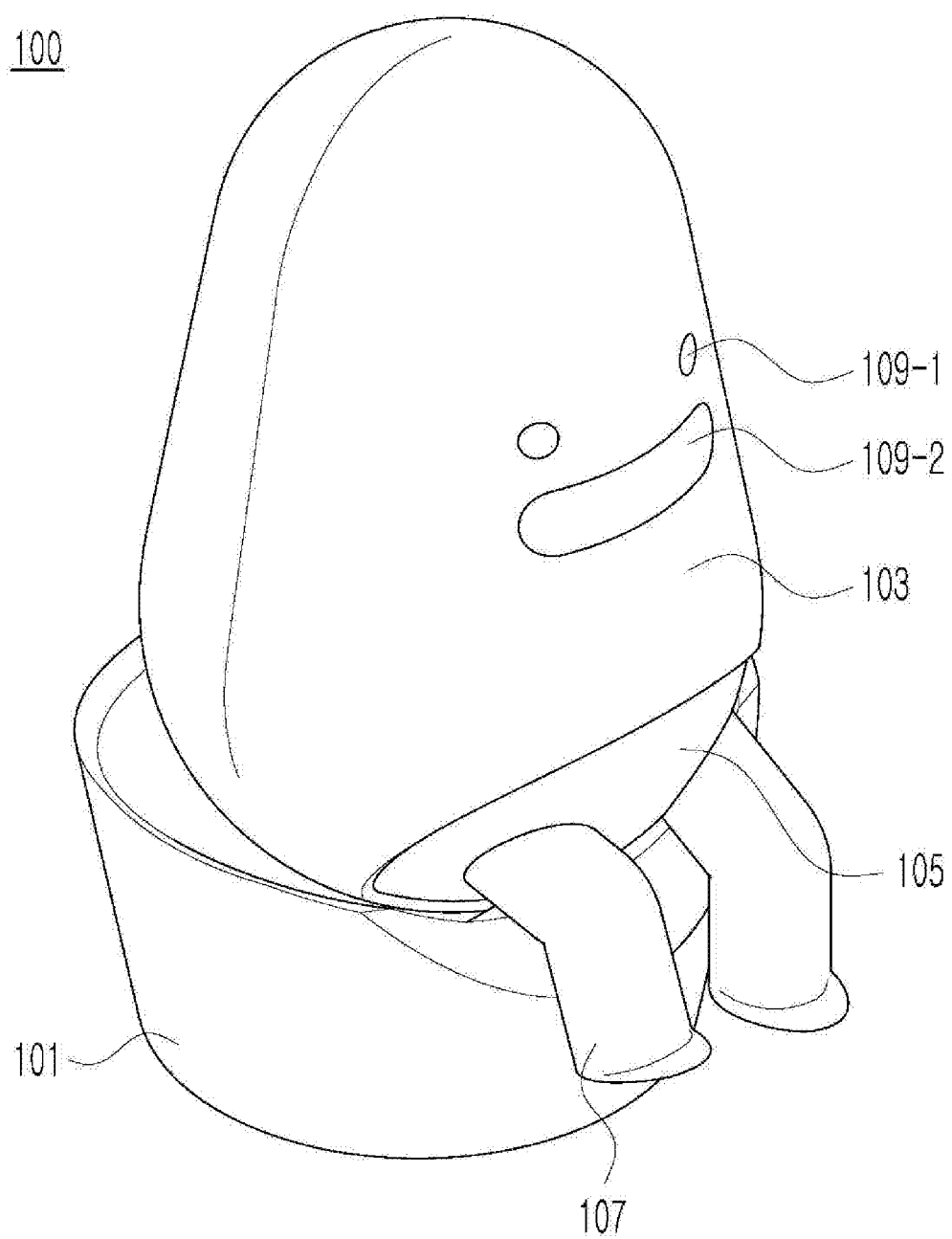
FIG. 12 is a reference diagram for schematically describing a configuration and an operation of a posture mimicking animated device.

FIG. 1 to FIG. 2C are diagrams for generally describing user interaction method and system using a posture recognition seat and a posture mimicking animated device according to an embodiment of the inventive concept. FIG. 3 is a reference diagram for describing a user posture recognition scheme via a posture recognition seat. FIG. 4 to FIG. 7 are reference diagrams for schematically describing interaction scenarios with a user according to an embodiment of the inventive concept. FIG. 8A to FIG. 11 are examples of an mobile application screen according to an embodiment of the inventive concept. FIG. 12 is a reference diagram for schematically describing a configuration and an operation of a posture mimicking animated device. Hereinafter, an embodiment of the inventive concept will be described in detail with reference to the accompanying drawings.

A user interaction system via user posture recognition according to an embodiment of the inventive concept may include a posture recognition seat, a posture mimicking animated device, and a mobile application [Refer to FIG. 1 to FIG. 2C].

Hereinafter, the user posture mimicking animated device having a shape of a doll that may be placed on the user's desk, and a seat on which the user sits having a posture recognition sensor will be mainly described. However, the inventive concept is not limited thereto, and various modifications thereof are possible. That is, a type (e.g., doll, toy, robot, etc.), a shape (e.g., human body, limb animal body, specific character body, etc.), a size, and behavior mimicking types and ranges of the user posture mimicking animated device to be described below may vary. Further, the posture recognition seat is not necessarily manufactured as an independent object such as a cushion or a memory foam, and may be manufactured as a seat as an accessory of a chair. In addition, it should be clear that the posture recognition sensor is not limited to a pressure sensor to be described below.

Further, hereinafter, referring to FIG. 1, an example in which communications occur between the posture recognition seat and the posture mimicking animated device, and between the posture recognition seat and the mobile application is described. However, various modifications thereof are possible. For example, the posture recognition seat, the posture mimicking animated device, and the mobile application may be connected to each other for communication. Information obtained from the posture recognition seat may be transmitted to the mobile application through the posture mimicking animated device or vice versa.

Further, hereinafter, referring to FIG. 1, an example in which state information (i.e., posture value) about a sitting posture of the user as obtained (determined) from the posture recognition seat is transmitted to the posture mimicking animated device and the mobile application will be mainly described. However, various modifications thereof are possible. For example, the posture recognition seat may transmit only sensing result information collected by the posture recognition sensor to the posture mimicking animated device and the mobile application, and actual posture determination may be performed directly by the posture mimicking animated devices and the mobile application.

Further, in FIG. 1, it is shown that RF communication occurs between the posture recognition seat and the posture mimicking animated device, while Bluetooth communication occurs between the posture recognition seat and the mobile application. However, the present disclosure is not limited thereto. In another example, communication thereof with other external devices (e.g., a server, etc.) may be performed.

However, hereinafter, for convenience and concentration of description, each of the major components of the inventive concept will be described sequentially based on the embodiment shown in FIG. 1 and FIG. 2A to 2C as an embodiment of the inventive concept.

Posture Recognition Seat

In an embodiment of the inventive concept, the posture recognition seat includes a posture recognition sensor for recognition of a sitting posture of the user, and includes at least one communication module for communication with an external device.

More specifically, the posture recognition seat may include the posture recognition sensor including a plurality of pressure sensors spaced apart from each other so that an entirety of a seated surface of the seat is covered with the plurality of pressure sensors; a posture recognition module that determines a current sitting posture of the user based on a plurality of sensed values acquired by the plurality of pressure sensors to obtain state information about the determined sitting posture; and at least one communication module that transmits the state information obtained from the posture recognition module to each of the posture mimicking animated device and the mobile application.

In this connection, the number and installation position of the pressure sensors installed inside the posture recognition seat may vary. However, in one example, FIG. 3 illustrates a case where a total of six pressure sensors are distributed in the seat.

In this connection, the posture recognition module may compare the obtained plurality of sensed values with a posture table storing, therein, information pre-classified based on the state of the sitting posture of the user to obtain the state information about the sitting posture of the user.

In more detail, according to an embodiment, when a pressure is sensed by the plurality of pressure sensors, the posture recognition module may sample the detected data at a preset time interval and may calculate sampling data having the detected pressure value equal to or greater than a specific threshold as valid data, and may convert the valid data into metadata of a preset data structure (in one example, including fields such as received time information, position information of a center of a region in which the pressure is detected, pressure value information, etc.), and may compare information included in the meta data with a plurality of object information on the pre-stored posture table and determine the sitting posture of the user based on the comparison result. In this connection, when the determined posture lasts for a larger time duration than a preset time duration, the state information on the posture may be transmitted to the posture mimicking animated device and the mobile application.

In this connection, the state information about the sitting posture as determined may include posture values that indicate a correct-posture sitting state, a left-inclined sitting state, a right-inclined sitting state, a front-inclined sitting state, a rear-inclined sitting state, and a legs-crossing sitting state [see FIG. 3]. In another example, in addition to the above sitting states, various state information may be classified and obtained. In the present specification, only the six postures as described above (that is, the correct-posture sitting state as a correct posture and the remaining five sitting states as the incorrect posture) are set forth for convenience and concentration of description.

Further, according to the embodiment of the inventive concept, a weight of the user, an area of an occupied surface when sitting on the seat may vary based on the user. Thus, the posture recognition seat may include a function of resetting an initial pressure value so that individually customized setting thereof is realized [see FIG. 4].

Posture Mimicking Animated Device

In an embodiment of the inventive concept, the posture mimicking animated device includes a communication module for performing communication with the communication module of the posture recognition seat. The posture mimicking animated device may visually mimic or visually or audibly guide the sitting posture of the user based on the state information about the sitting posture of the user received from the posture recognition seat [see FIG. 5 and FIG. 6].

To this end, as in an example of FIG. 12, a posture mimicking animated device 100 may include a lower body 105; an upper body 103 coupled to a top of the lower body; legs 107 respectively coupled to both sides of the lower body; a supporter 101 on which the lower body is seated; and a posture mimicking controller (not shown, and implemented as a control board).

In this connection, the upper body 103 is coupled to the lower body 105 via a front/rear/left/right four-directional motor. Thus, under motor control of the posture mimicking controller, the upper body 103 performs a rolling rotation relative to the lower body 105 so that the left-inclined sitting state and the right-inclined sitting state may be implemented. Further, the upper body 103 performs a pitching rotation relative to the lower body 105 so that the front-inclined sitting state and the rear-inclined sitting state may be implemented. In this connection, the pitching/rolling rotations of the upper body 103 may be performed within a predetermined angular range (e.g., ±15° range), such that the posture mimicking animated device mimics the front/rear/left/right inclined sitting states.

Further, the legs 107 extend toward an outer surface of the supporter 101 and are suspended so as not to touch a ground on which the supporter 101 is placed, and is coupled to the lower body 105 via a motor to perform a rolling rotation relative to the lower body 105 under the motor control of the posture mimicking controller such that the legs-crossing sitting state may be implemented. In this connection, the rolling rotation of the legs 107 may be performed at a predetermined angle (e.g., 90°), thereby to mimic the legs-crossing state.

Further, the posture mimicking animated device 100 has face-shaped portions 109-1 and 109-2 made of a light-transmitting material and shaping a face and disposed on an upper front side of the upper body 103. Color light emitting modules (not shown) may be disposed inside the upper body in positions corresponding to the face-shaped portions, respectively.

Accordingly, under control of light emission of the color light emitting modules by the posture mimicking controller, a predetermined color corresponding to state information on the sitting posture is rendered through the face-shaped portions, such that the state information about the sitting posture may be visually recognized by the user. In one example, in order that a specific posture state may be visually recognized through the face-shaped portions, green or blue light may be output in the correct posture while red light may be output in the incorrect posture. Although not clearly shown on the drawings attached to the present specification, a specific facial expression pattern of the face-shaped portions may be implemented. For example, a smiling facial expression may be implemented in the correct posture, while an angry facial expression or a gloomy facial expression may be implemented in the incorrect posture.

The posture mimicking animated device as described above allows the user to self-recognize the posture thereof. Thus, when the incorrect posture persists, the movement of the doll and the change in the face color thereof may notice the user of the incorrect posture.

Further, although not clearly shown on the drawings attached to the present specification, a Bluetooth speaker, etc. may be mounted on a portion (e.g., the supporter 101 in FIG. 12) of the posture mimicking animated device, thereby to inform the user of the sitting posture status of the user in an audible manner such as voice or sound. For example, when the incorrect posture status is maintained for a long time, a pre-stored sound (sigh, crying, voices of acquaintance, etc.) may be output.

In addition, a camera may be mounted on another portion of the posture mimicking animated device to implement a function for monitoring the user. For example, the device may monitor the user's posture and facial emotion changes using the camera sensor and may present an application screen corresponding to an emotion based on an individual situation, and a color that may stabilize a heart of the user.

Mobile Application

According to an embodiment of the inventive concept, the mobile application may be installed in a communication device possessed by the user, and receive synchronized information related to the sitting posture of the user through communication with the posture recognition seat, and create user interaction information corresponding to the received information and display the information through the application screen.

The mobile application may display a two-dimensional or three-dimensional animation object having the same shape as that of the posture mimicking animated device on the application screen. The mobile application may allow the animation object visualizing the posture mimicking animated device to be processed to express a visual effect consistent with mimicking motion and color lighting of the posture mimicking animated device based on the synchronized information received from the posture recognition seat [See FIG. 9 to FIG. 11].

Further, the mobile application may display additional information related to the sitting posture of the user on the application screen. In this connection, the additional information may include a sitting time duration, a temporal percentage of each posture for the sitting time duration, a period-specific statistics about the temporal percentage, user's health state information based on the sitting posture (e.g., information about an effect of the sitting posture on the user's health), information about disease/disorder having high onset probability depending on the sitting posture, disease/disorder incidence statistics, etc. [See FIG. 7 to FIG. 8C].

Further, when information on whether the user has sat on the seat is not received from the posture recognition seat at an appointment time set as a time when the user should sit thereon or a corresponding registration schedule of the user, the mobile application may display a predetermined visual effect for indicating that the appointment or the schedule is not conducted through the animation object. For example, the visual effect may include an appearance in which the animation object visualizing the posture mimicking animated device bows a head, a sullen facial expression, and low-saturation color lighting. The same may be applied to the posture mimicking animated device.

Similarly, when information on whether the user has sat on the seat is received from the posture recognition seat at an appointment time set as a time when the user should sit thereon or a corresponding registration schedule of the user (i.e., when the appointment is conducted), or when information on whether the user has sat is received from the posture recognition seat at a time spaced by a predetermined reference period or greater from the appointment time (i.e., when the user sits on the east after a long time), the mobile application may present a pre-specified visual effect to indicate that the appointment or the schedule is conducted or to encourage the user to sit on the seat on the appointment time through the animation object. The visual effect may include a greeting gesture to express welcome, blinking or lighting). This may also be applied to the posture mimicking animated device.

Further, when communication based association between a communication device designated by the user and the mobile application is made, the mobile application may present a pre-designated visual effect associated with a notification message received by the communication device designated by the user through the animation object. This may also be applied to the posture mimicking animated device.

FIG. 4 to FIG. 7 are reference diagrams for schematically describing interaction scenarios with the user according to an embodiment of the inventive concept.

Figure 4:
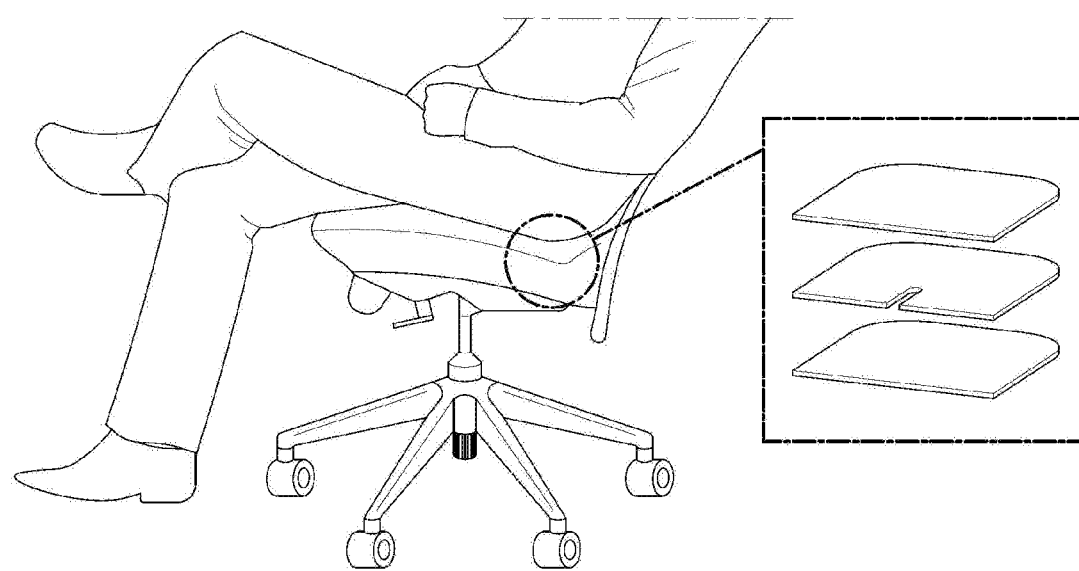
FIG. 4 to FIG. 7 are reference diagrams for schematically describing interaction scenarios with a user according to an embodiment of the inventive concept.

Referring to FIG. 4, the system according to the inventive concept receives an initial value for smooth interaction with the user. Further, the system may allow the user to sit on the seat in the correct posture and conduct simple personalization via a push of a button.

Figure 5:
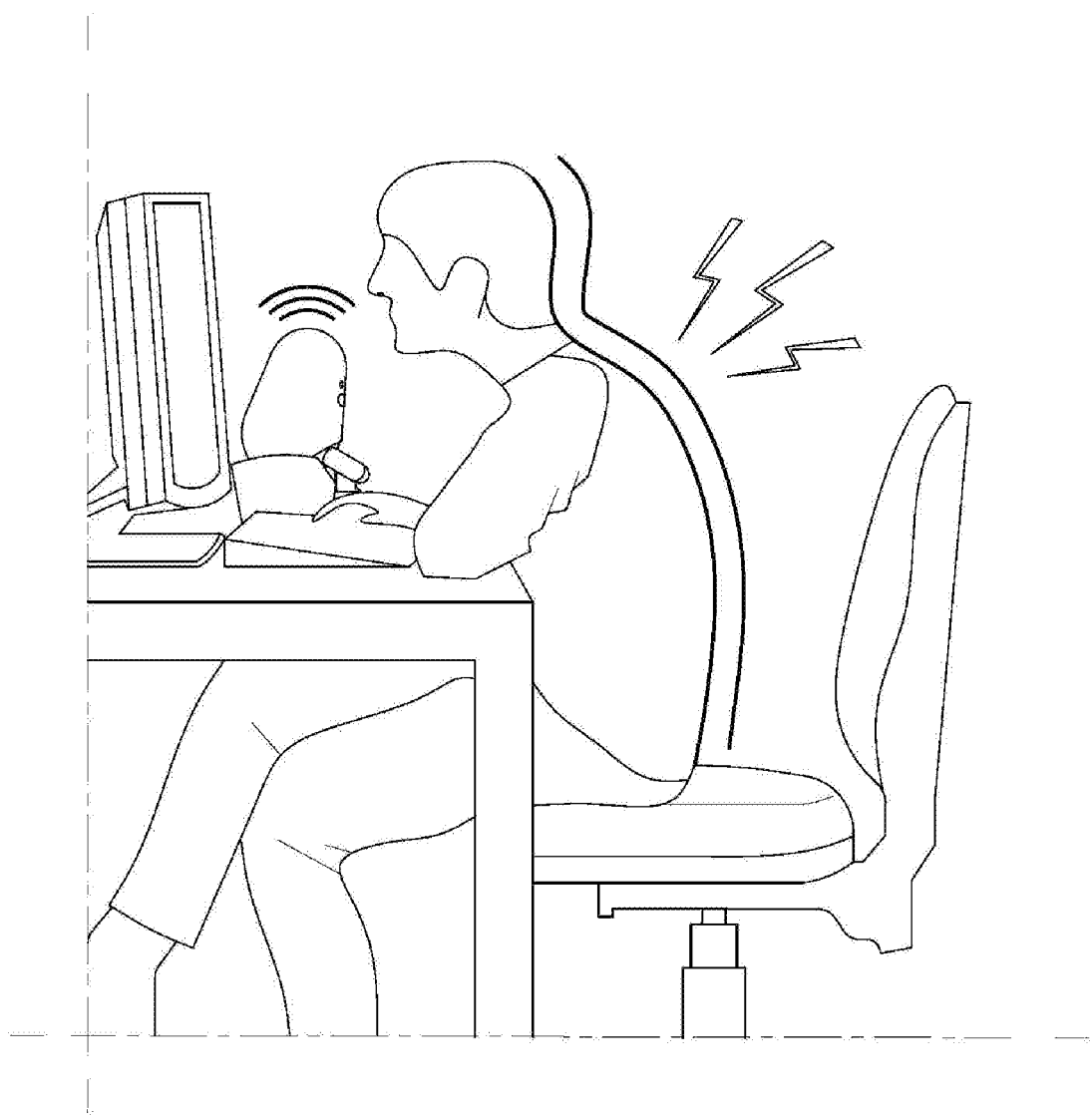

Referring to FIG. 5, the system according to the inventive concept may determine that the user sits on the seat in the incorrect posture for a certain period of time, and may allow Baro (a brand name of the posture mimicking animated device) to mimic the user.

Figure 6:
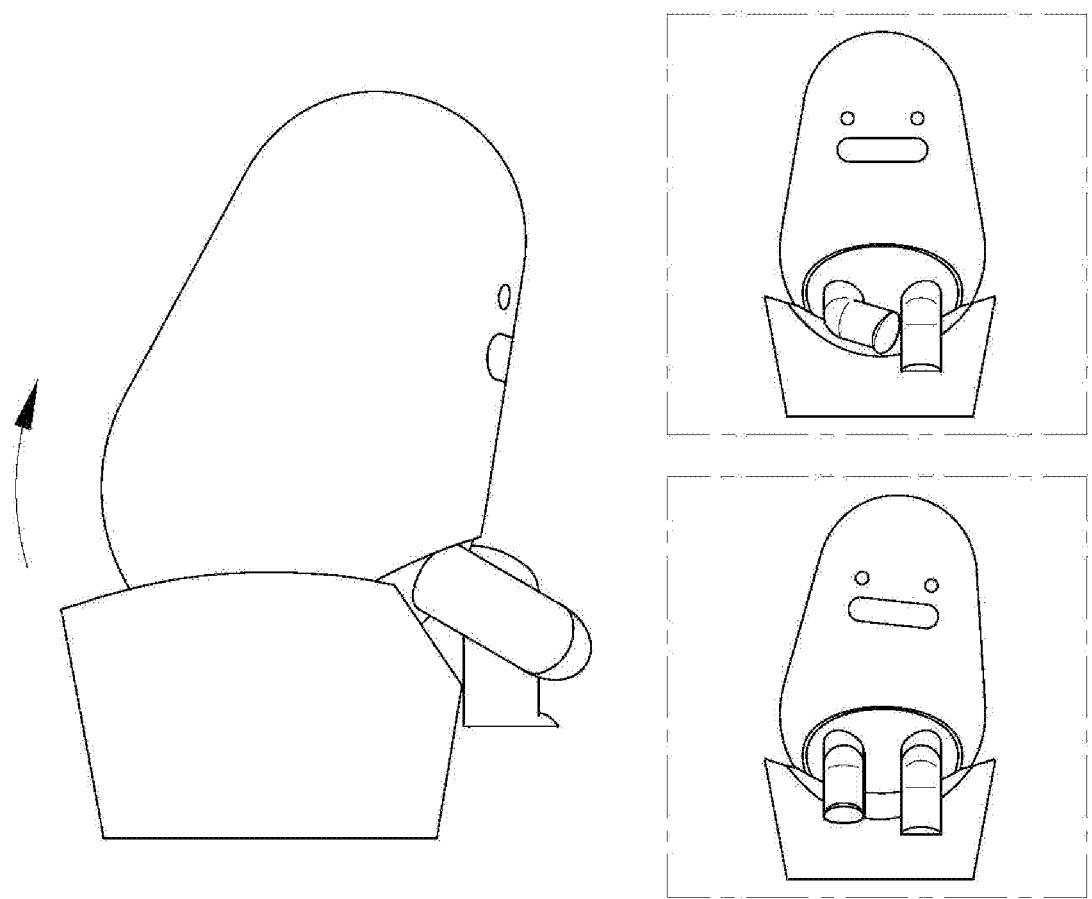

Referring to FIG. 6, the system according to the inventive concept may allow the Baro to mimic the user's posture so that the user recognizes his or her posture and sits thereon correctly. The Baro may mimic the user's posture such as the front, rear, left or right inclined posture or the legs-crossing posture. The Baro's facial light may change in the user's small movement as in a turtleneck state.

Figure 7:
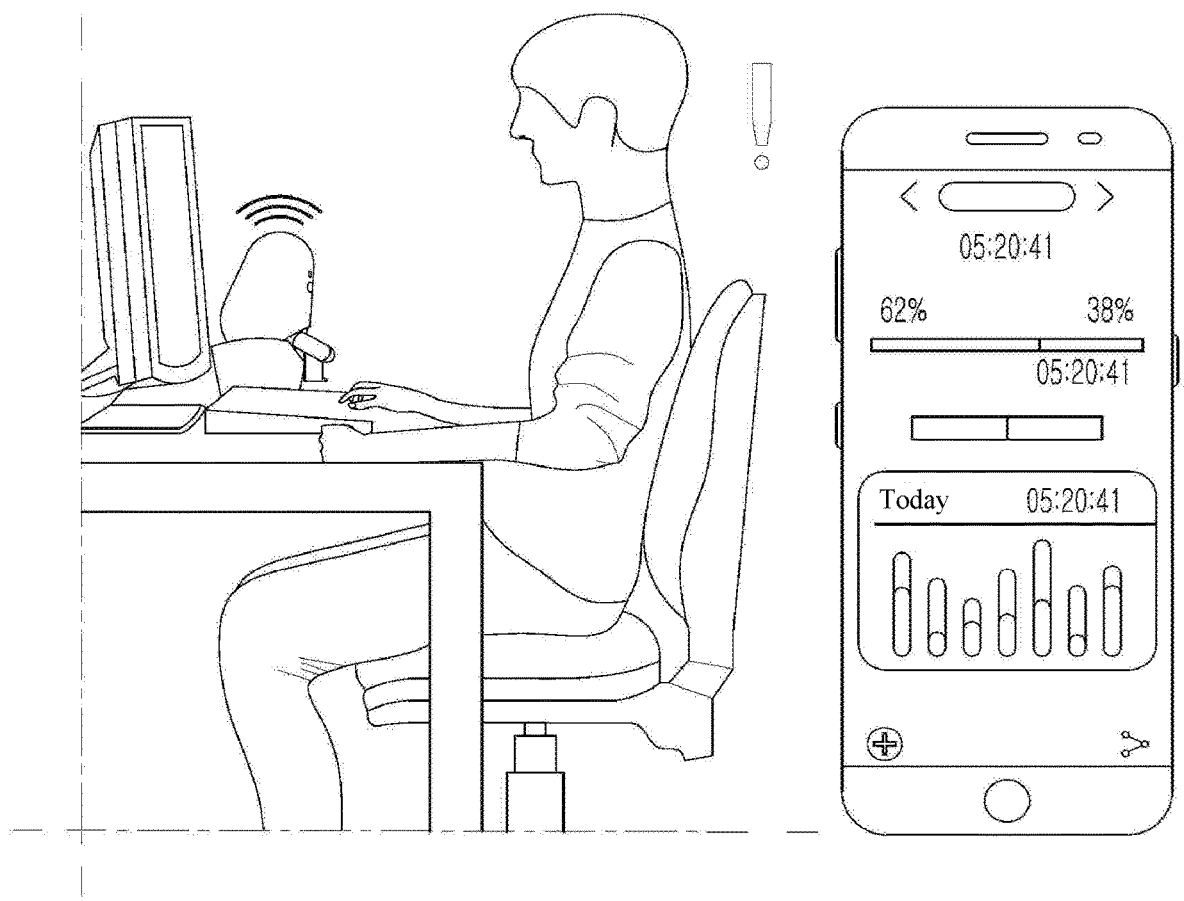
Figure 8A:
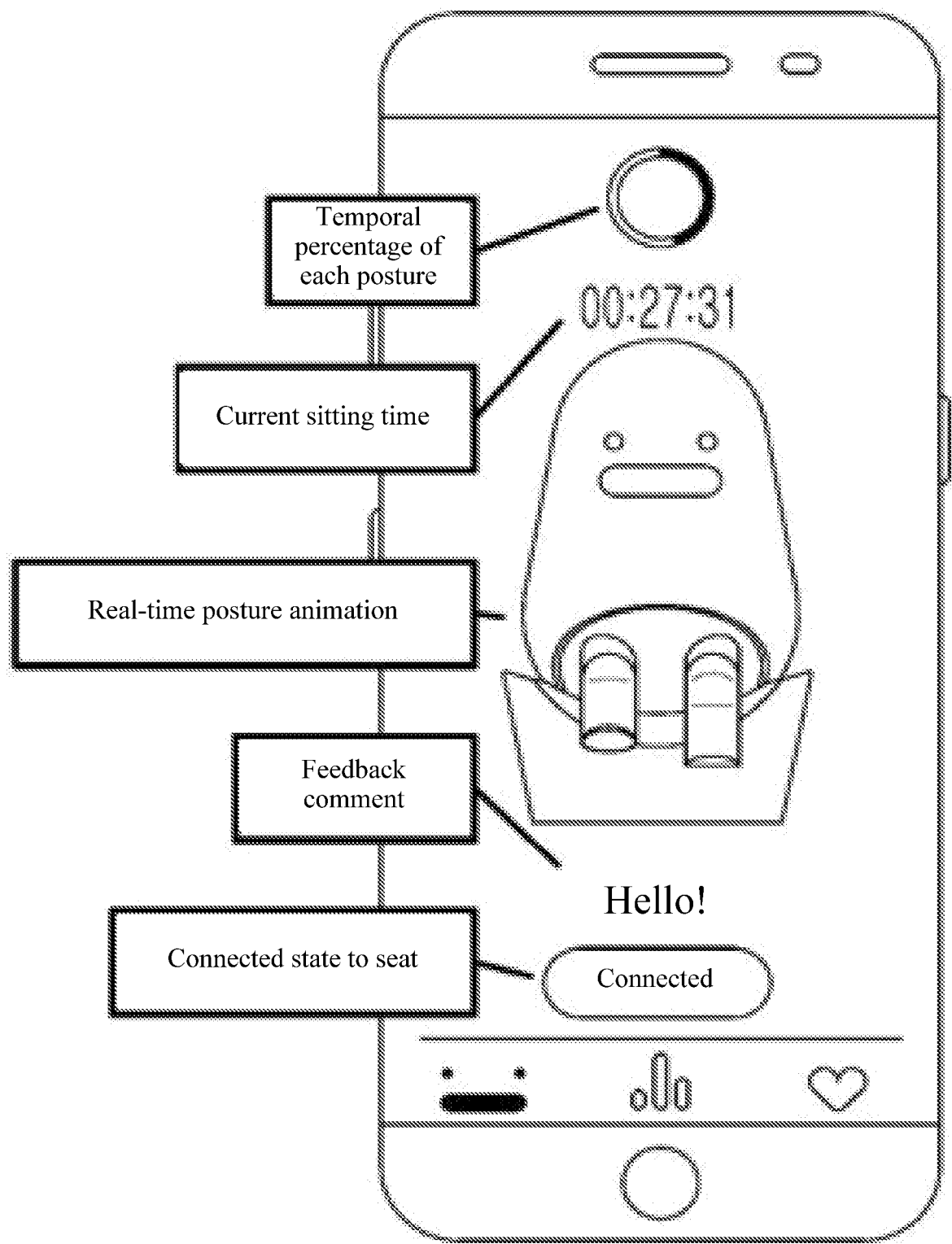
FIG. 8A to FIG. 11 are examples of an mobile application screen according to an embodiment of the inventive concept.
Figure 8B:
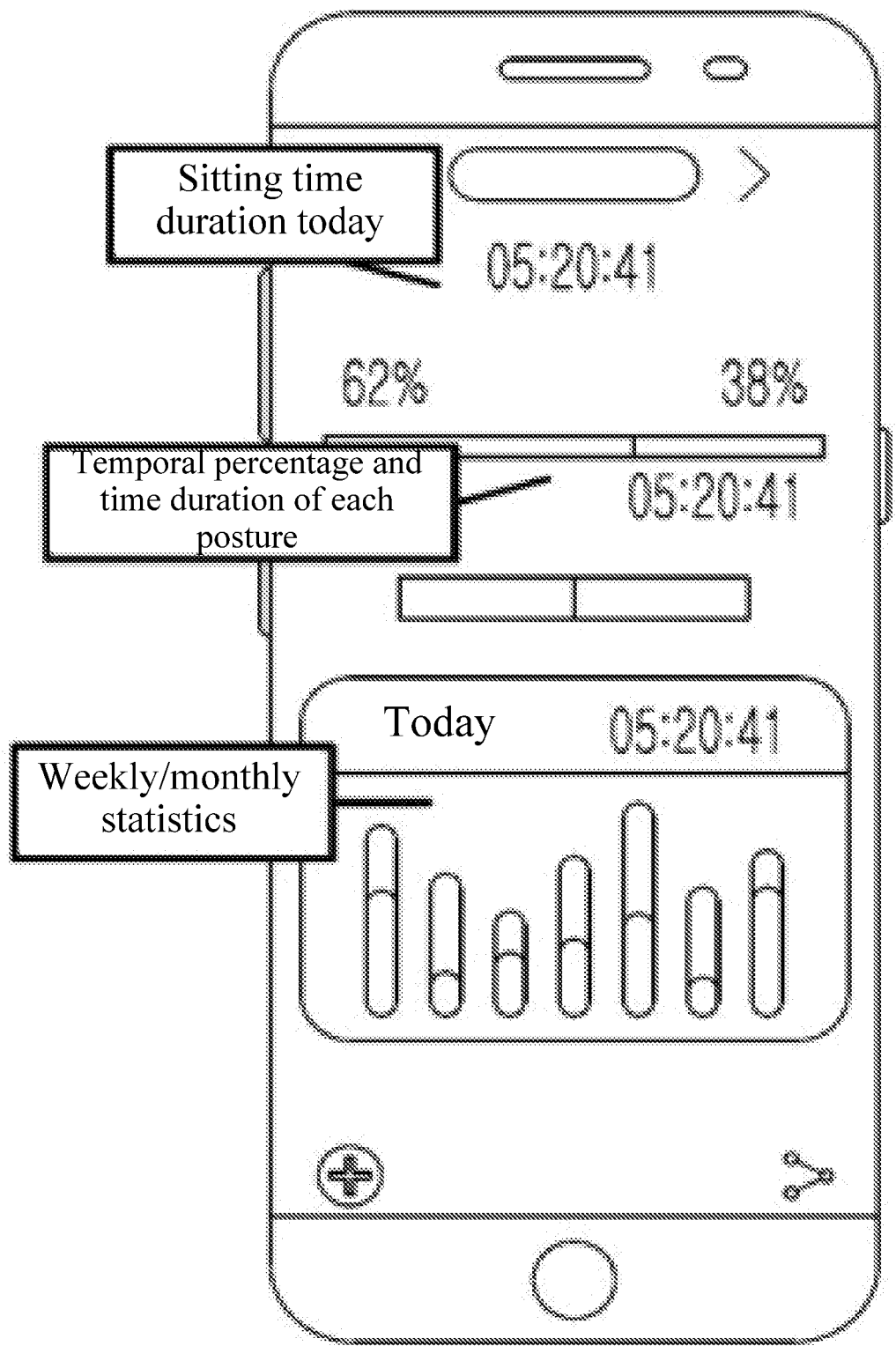
Figure 8C:
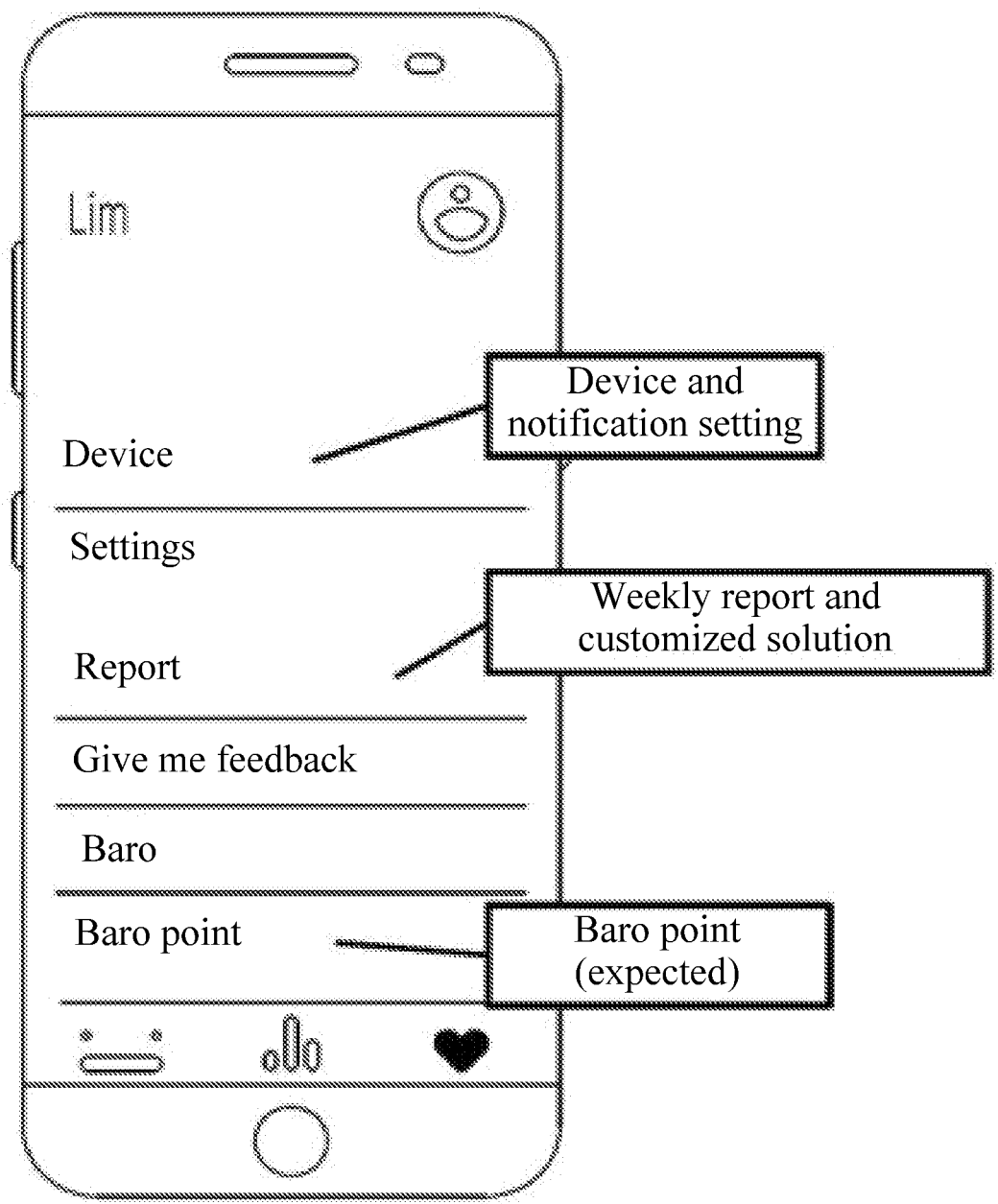
Figure 9:
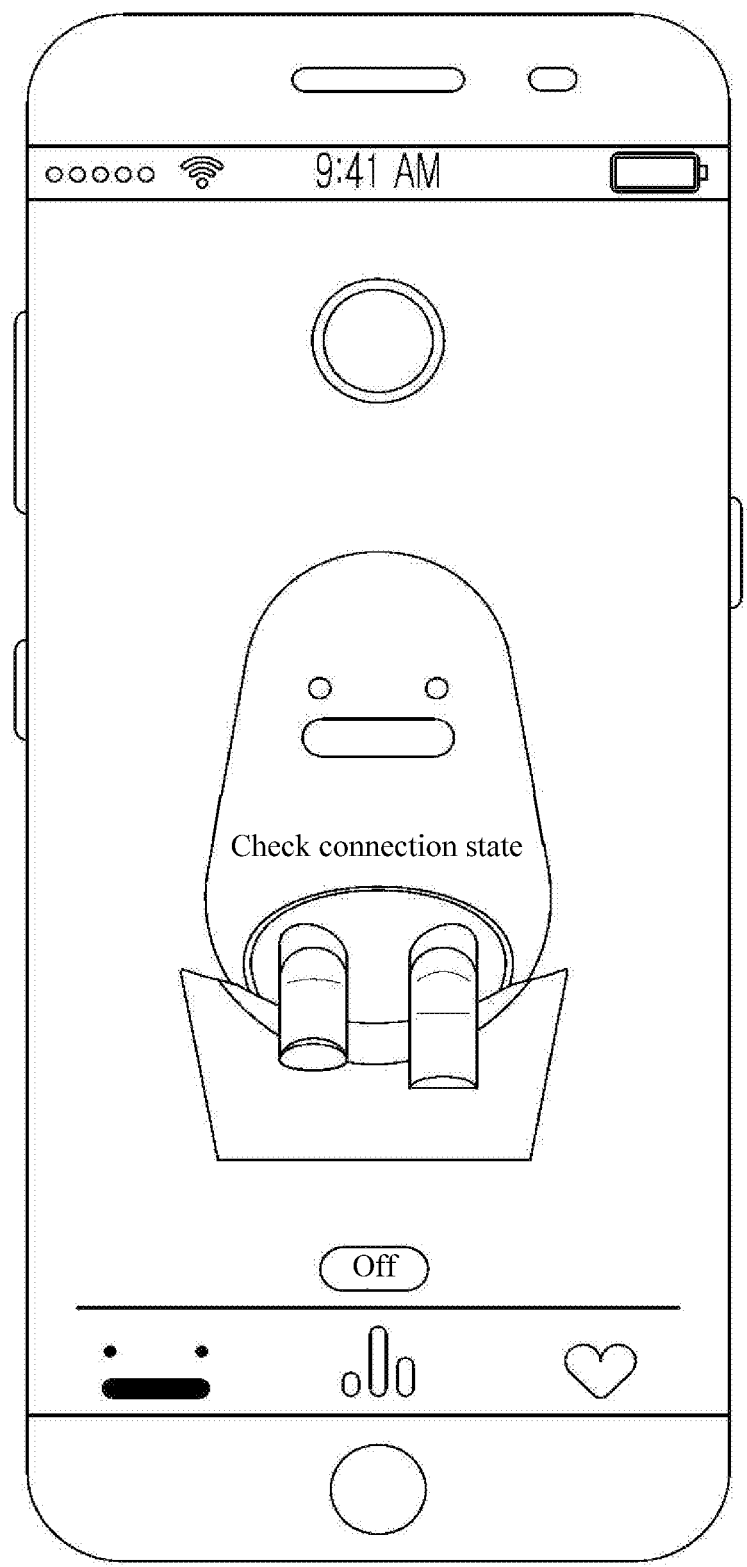
Figure 10:
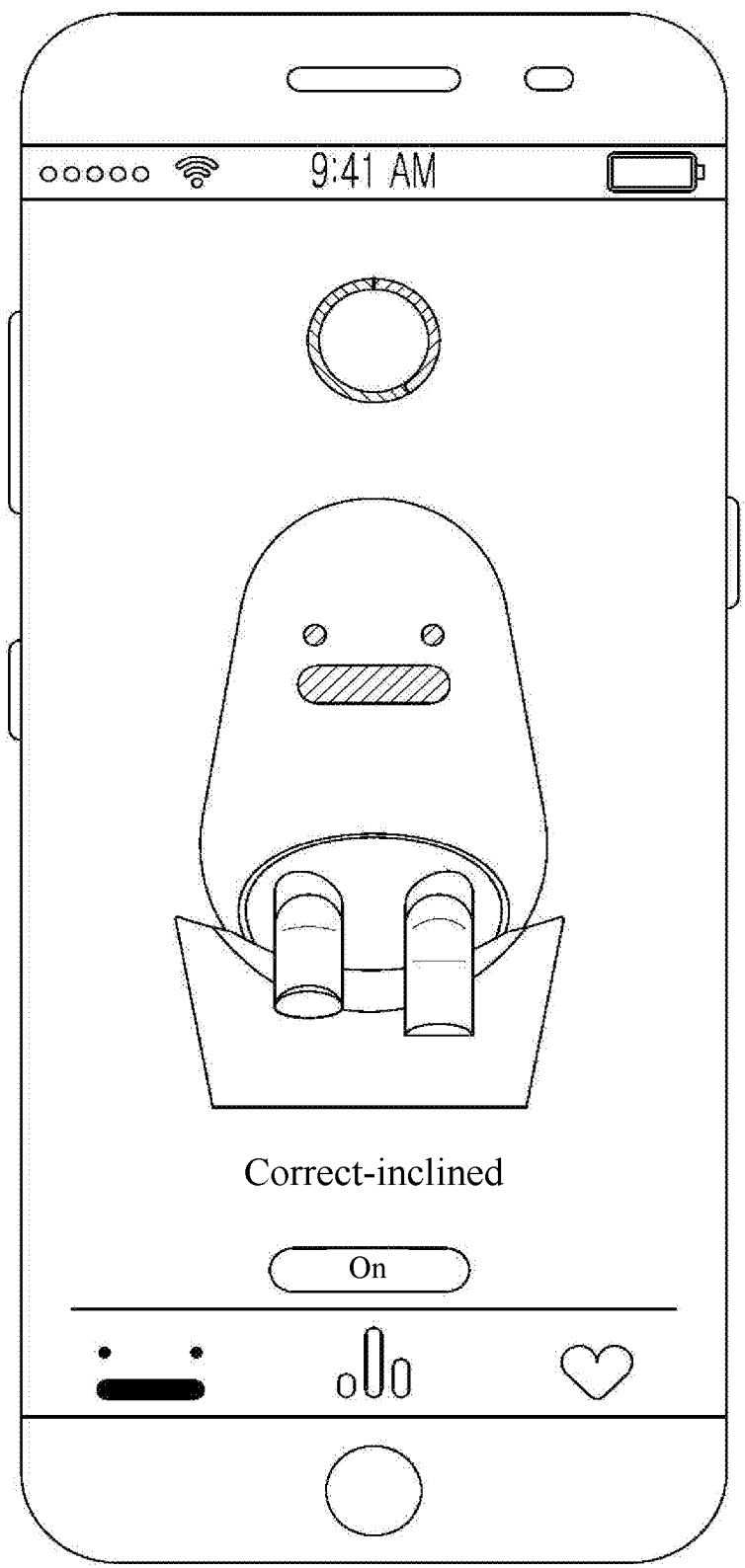
Figure 11:
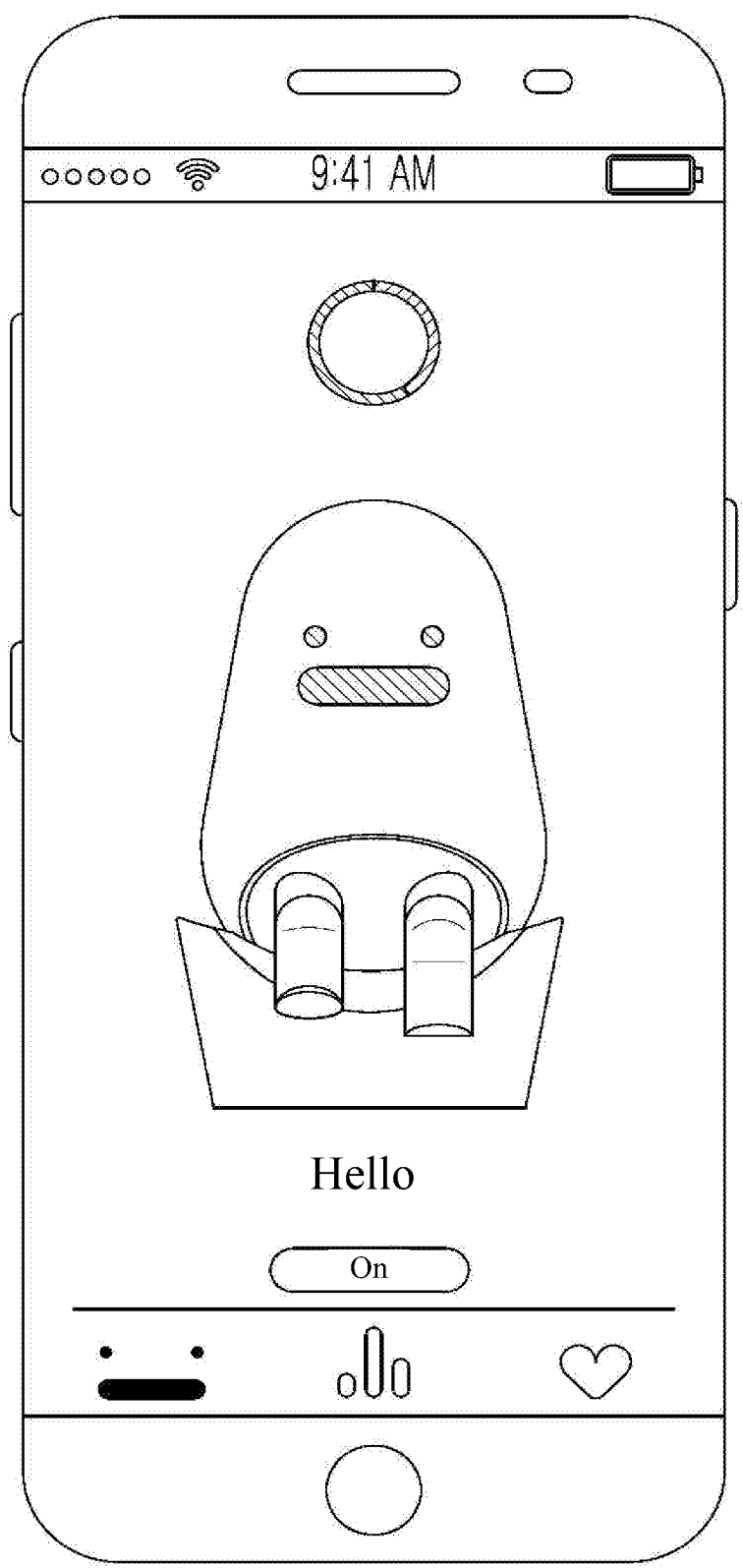

Referring to FIG. 7, the user visually checks that the Baro mimics his or her incorrect posture and may correct the incorrect posture to sit thereon correctly. Personal posture data (temporal percentage of each posture per day, week, and month) may be managed through the application.

The user interaction method using the posture recognition seat and the posture mimicking animated device according to the embodiment of the inventive concept as described above may be implemented using a computer-readable code on a computer-readable recording medium. The computer-readable recording media may include all types of recording media in which data that may be decoded by a computer system are stored. For example, the media may include read only memory (ROM), random access memory (RAM), a magnetic tape, a magnetic disk, a flash memory, an optical data storage device, and the like. Further, the computer-readable recording medium may be distributed in computer systems connected to each other via a computer communication network, and stored and executed as codes that may be read in a distributed scheme.

The user interaction method and system using the posture recognition seat and the posture mimicking animated device according to an embodiment of the inventive concept may allow the user to continuously recognize the posture thereof and voluntarily correct the posture, and may induce interest through the interaction with the user using the posture mimicking animated device, and may continuously maintain a frequency of use thereof using the animated device having diversified sounds or suitable for the taste of consumers.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A user interaction system for performing interaction with a user based on recognition of a sitting posture of the user, the system comprising:
  a posture recognition seat including a posture recognition sensor for recognition of the sitting posture of the user, and at least one communication module for communication with an external device;
  a posture mimicking animated device including a communication module for performing communication with the communication module of the posture recognition seat, wherein the posture mimicking animated device visually mimics the sitting posture of the user or visually or audibly guide the sitting posture of the user, in accordance with state information about the sitting posture of the user determined based on a sensing result obtained by the posture recognition sensor; and
  a mobile application installed in a communication device possessed by the user, wherein the mobile application receives synchronized information related to the sitting posture of the user via communication with the posture recognition seat, and generates user interaction information corresponding to the received information and displays the user interaction information on an application screen,
  wherein the posture recognition seat includes:
  the posture recognition sensor including a plurality of pressure sensors spaced apart from each other so that an entirety of a seated surface of the seat is covered with the plurality of pressure sensors;
  a posture recognition module configured to determine a current sitting posture of the user based on a plurality of sensed values acquired by the plurality of pressure sensors to obtain state information about the determined sitting posture; and
  the at least one communication module configured to transmit the state information obtained from the posture recognition module to each of the posture mimicking animated device and the mobile application,
  wherein the posture recognition module is configured to compare the obtained plurality of sensed values with a posture table storing, therein, information pre-classified based on the state of the sitting posture of the user to obtain the state information about the sitting posture of the user,
  wherein the state information includes posture values that indicate a correct-posture sitting state, a left-inclined sitting state, a right-inclined sitting state, a front-inclined sitting state, a rear-inclined sitting state, and a legs-crossing sitting state,
  wherein the posture mimicking animated device includes a lower body; an upper body coupled to a top of the lower body; legs respectively coupled to both sides of the lower body; a supporter on which the lower body is seated; and a posture mimicking controller, wherein the upper body is coupled to the lower body via a motor and, thus, under motor control of the posture mimicking controller, performs a rolling rotation relative to the lower body so that the left-inclined sitting state and the right-inclined sitting state are implemented, and performs a pitching rotation relative to the lower body so that the front-inclined sitting state and the rear-inclined sitting state are implemented, wherein the legs extend toward an outer surface of the supporter and are suspended so as not to touch a ground on which the supporter is placed, and is coupled to the lower body via a motor to perform a rolling rotation relative to the lower body under the motor control of the posture mimicking controller such that the legs-crossing sitting state is implemented, wherein the posture mimicking animated device includes:
face-shaped portions made of a light-transmitting material and shaping a face and disposed on an upper front side of the upper body; and
color light emitting modules disposed inside the upper body in positions corresponding to the face-shaped portions, respectively, wherein under control of light emission of the color light emitting modules by the posture mimicking controller, a predetermined color corresponding to the state information on the sitting posture is rendered through the face-shaped portions, such that the state information about the sitting posture is visually recognized by the user, wherein the mobile application is configured to display a two-dimensional or three-dimensional animation object having the same shape as a shape of the posture mimicking animated device on the application screen, wherein the mobile application is configured to allow the animation object visualizing the posture mimicking animated device to be processed to express a visual effect corresponding to mimicking motion and color lighting of the posture mimicking animated device based on the synchronized information received from the posture recognition seat, wherein the mobile application is configured to display additional information related to the sitting posture of the user on the application screen, wherein the additional information includes at least one of a sitting time duration, a temporal percentage of each posture for the sitting time duration, a period-specific statistics about the temporal percentage, or user's health state information based on the sitting posture, wherein when information on whether the user has sat on the seat is not received from the posture recognition seat at an appointment time set as a time when the user should sit thereon or a corresponding registration schedule of the user, the posture mimicking animated device or the mobile application is configured to display a predetermined visual effect for indicating that the appointment or the schedule is not conducted through the animation object or the posture mimicking animated device.

2. The system of claim 1, wherein when information on whether the user has sat on the seat is received from the posture recognition seat at the appointment time set as a time when the user should sit thereon or the corresponding registration schedule of the user, or when information on whether the user has sat is received from the posture recognition seat at a time spaced by a predetermined reference period or greater from the appointment time, the posture mimicking animated device or the mobile application is configured to present a pre-specified visual effect to indicate that the appointment or the schedule is conducted or to encourage the user to sit on the seat on the appointment time through the animation object or the posture mimicking animated device.

3. The system of claim 1, wherein when communication-based association between a communication device designated by the user and the posture mimicking animated device or the mobile application is established, the posture mimicking controller or the mobile application is configured to present a pre-designated visual effect associated with a notification message received by the communication device designated by the user through the animation object or the posture mimicking animated device.

* * * * *